United States Patent
Mathiowitz et al.

(10) Patent No.: US 6,531,154 B1
(45) Date of Patent: Mar. 11, 2003

(54) MODULATED RELEASE FROM BIOCOMPATIBLE POLYMERS

(75) Inventors: Edith Mathiowitz, Brookline, MA (US); Wendy L. Webber, Foxboro, MA (US); Christopher G. Thanos, Providence, RI (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/093,868

(22) Filed: Jun. 9, 1998

Related U.S. Application Data

(60) Provisional application No. 60/050,946, filed on Jun. 10, 1997.

(51) Int. Cl.[7] .............. A61K 9/10; A61K 9/16; A61K 47/32; A61K 47/34; A61K 47/36
(52) U.S. Cl. .......... 424/487; 424/486; 424/488; 424/499; 424/501; 424/443; 424/426
(58) Field of Search ............... 424/487, 486, 424/501, 443–44, 449, 426, 428, 469–70, 457

(56) References Cited

U.S. PATENT DOCUMENTS

| | | | |
|---|---|---|---|
| 4,666,897 A | | 5/1987 | Golub et al. |
| 4,919,939 A | | 4/1990 | Baker |
| 5,120,548 A | * | 6/1992 | McClelland et al. |
| 5,502,042 A | * | 3/1996 | Barrows et al. |
| 5,514,378 A | | 5/1996 | Mikos et al. |
| 5,656,297 A | | 8/1997 | Bernstein et al. |
| 5,674,534 A | | 10/1997 | Zale et al. |
| 5,716,644 A | | 2/1998 | Zale et al. |
| 5,741,524 A | * | 4/1998 | Staniforth et al. |

FOREIGN PATENT DOCUMENTS

WO  WO95/29664  11/1995

OTHER PUBLICATIONS

Amsden and Cheng, "A generic protein delivery system based on osmotically rupturable monoliths," *J. Controlled Release.* 33:99–105 (1995).
Dordunoo et al., "Release of taxol from poly(E–caprolactone) pastes: effect of water–soluble additives," *J. Controlled Release.* 44, 87–94 (1997).

* cited by examiner

*Primary Examiner*—Edward J. Webman
(74) *Attorney, Agent, or Firm*—Holland & Knight LLP

(57) ABSTRACT

Sustained delivery compositions which modulate the release of incorporated prophylactic, therapeutic, and/or diagnostic agents, and methods of preparation and use thereof, are disclosed. The compositions include a biocompatible polymeric matrix; a prophylactic, therapeutic, and/or diagnostic agent dispersed within the polymeric matrix; and a monovalent cation component which is separately dispersed within the polymeric matrix. The monovalent cation component modulates the release of the incorporated agent from the polymeric matrix. The compositions can be prepared by dissolving a biocompatible polymer in a solvent to form a polymer solution, and separately dispersing a monovalent cation and a prophylactic, therapeutic, and/or diagnostic agent within the polymer solution. The polymer solution is then solidified to form a polymeric matrix, wherein a significant amount of the monovalent cations is dispersed in the polymeric matrix separately from the incorporated agent. The cation modulates the release of the incorporated agent from the polymeric matrix.

19 Claims, 8 Drawing Sheets

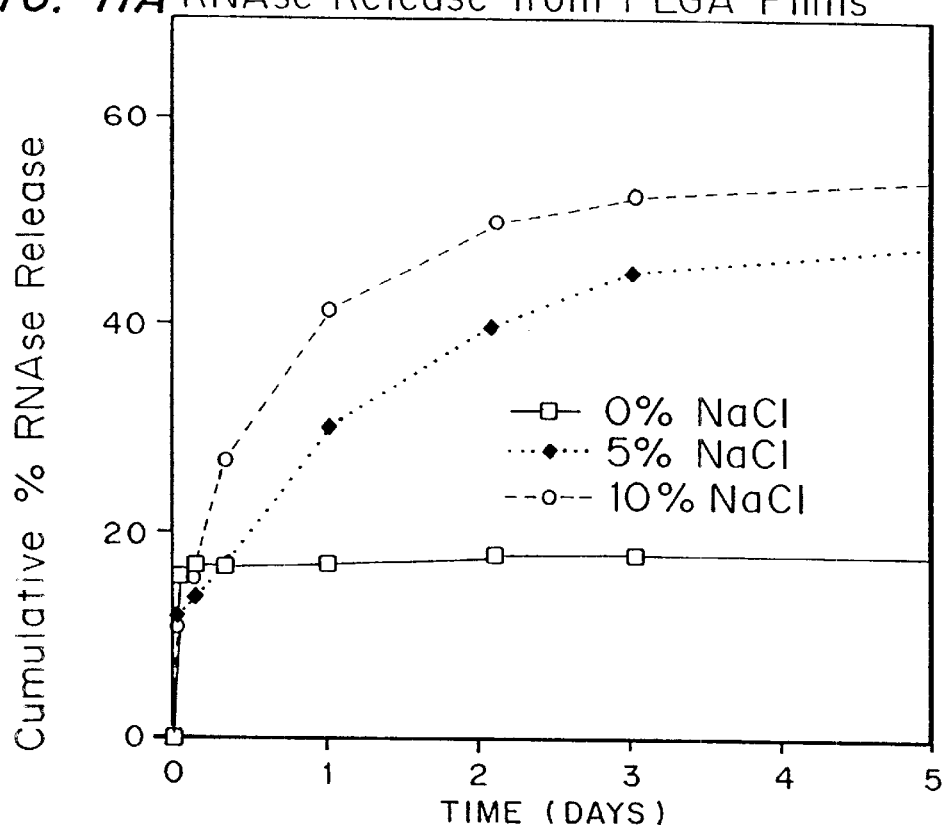
FIG. 11A RNAse Release from PLGA Films
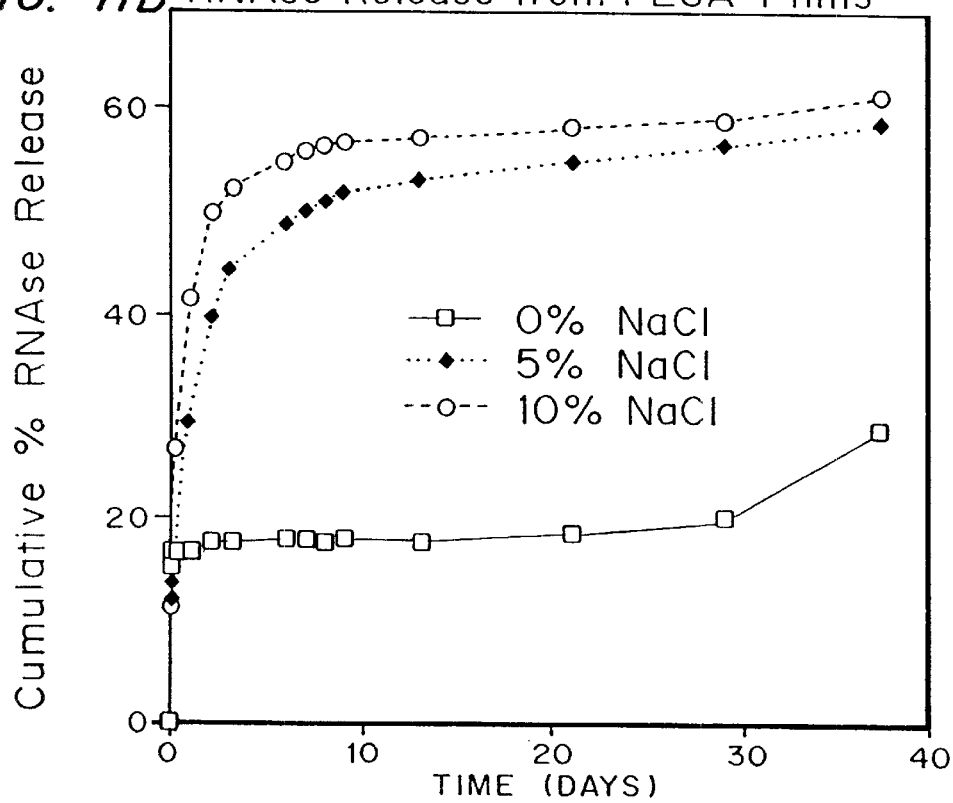
FIG. 11B RNAse Release from PLGA Films

MODULATED RELEASE FROM BIOCOMPATIBLE POLYMERS

CROSS-REFERENCE TO RELATED APPLICATIONS

Priority is claimed to U.S. Provisional application Ser. No. 60/050,946, filed Jun. 10, 1997.

STATEMENT REGARDING FEDERALLY SPONSORED RESEARCH

Not applicable.

BACKGROUND OF THE INVENTION

Effective prophylactic or therapeutic treatment or diagnosis of many illnesses or conditions requires that a relatively constant level of therapeutic or diagnostic agents be administered in vivo. Before the development of timerelease delivery systems, prophylactic, therapeutic and diagnostic agents were commonly administered as several doses at regular intervals. However, this mode of administration provides fluctuating levels of these agents.

Sustained release formulations have been prepared to provide a relatively constant release of prophylactic, therapeutic and diagnostic agents. Some of these formulations use biodegradable substances, such as poly(lactide) (PLA) or poly(lactide-co-glycolide) (PLGA) microspheres or films containing the agent to be administered. A relatively steady release of incorporated agents is possible using these microspheres and/or films by taking advantage of the near linear degradation profile of these polymers. However, in some cases, the in vivo release of incorporated agents from biodegradable polymers is initially high or low, and therefore non-uniform throughout the life of the delivery device. Furthermore, some polymers can substantially degrade after a period of hydration, which can substantially limit the effective life of the controlled release devices. Accordingly, several attempts have been made to modulate the controlled release of incorporated agents from biodegradable polymers to provide a higher level of initial medicament release and to provide longer periods of fairly consistent medicament release levels in vivo.

U.S. Pat. No. 4,919,939 to Baker describes polymeric sustained release drug delivery systems for placement in the periodontal pocket. Baker's system incorporates drug-containing microparticles in a carrier medium and is effective for up to 30 days. However, a limitation of the device is that useful diffusion rates through the polymers are generally limited to drugs with molecular weights less than about 300.

U.S. Pat. No. 4,666,897 to Golub et al. teaches sustained release devices made from ethylene vinyl acetate (EVA) for sustained delivery of tetracycline. However, the EVA fibers are non-degradable and therefore must be physically removed after delivery of the therapeutic.

It is therefore an object of this invention to provide compositions for modulated release of an incorporated agent, wherein the composition includes a wide range of biocompatible polymers.

It is another object of this invention to provide biodegradable polymeric compositions for modulated release of an incorporated agent.

SUMMARY OF THE INVENTION

Sustained delivery compositions which modulate the release of incorporated prophylactic, therapeutic and/or diagnostic agents, and methods of preparation and use thereof, are disclosed. The compositions include a biocompatible polymeric matrix, a prophylactic, therapeutic, and/or diagnostic agent dispersed within the polymeric matrix, and a monovalent cation component which is separately dispersed within the polymeric matrix. The monovalent cation component modulates the release of the incorporated agent from the polymeric matrix.

The compositions can be prepared by dissolving a biocompatible polymer in a solvent to form a polymer solution, and separately dispersing a monovalent cation and a prophylactic, therapeutic, and/or diagnostic agent within the polymer solution. The polymer solution is then solidified to form a polymeric matrix. At least a significant amount of the monovalent cations is dispersed in the polymeric matrix separately from the incorporated agent. The cation modulates the release of the incorporated agent from the polymeric matrix.

BRIEF DESCRIPTION OF THE DRAWINGS

FIG. 1A shows the first five days of tetracycline release, while the FIG. 1B shows the release over the first 50 days of tetracycline release.

FIGS. 11A and 11B are graphs showing the cumulative release of RNAse (%) as a function of time for PLGA polymer films loaded with 10% RNAse and 0, 5, and 10% NaCl by weight.

DETAILED DESCRIPTION OF THE INVENTION

Figure 1A:
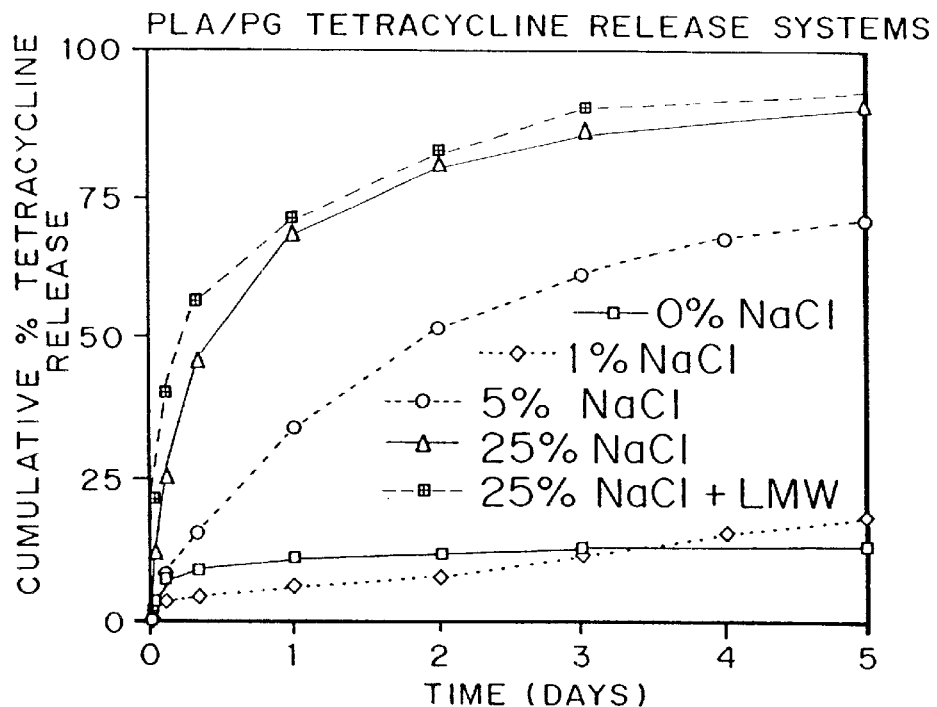
FIGS. 1A and 1B show the cumulative percent (%) of tetracycline released into PBS buffer at 37° C. as a function of time (days). Black squares represent poly (lactide-co-glycolide) (hereinafter "PLGA") solvent cast film loaded with 5% tetracycline (w/w), 0% NaCl. Diamonds represent PLGA film with 1% NaCl and 5% tetracycline. Circles represent PLGA film with 5% NaCl and 5% tetracycline. Triangles represent PLGA film with 25% NaCl and 5% tetracycline. Grey squares represent PLGA film with 25% NaCl, low molecular weight excipient and 5% tetracycline.

Sustained delivery compositions which modulate the release of incorporated prophylactic, therapeutic and/or diagnostic agents, and methods of preparation and use thereof, are disclosed. The compositions include a biocompatible polymeric matrix; a prophylactic, therapeutic, and/or diagnostic agent dispersed within the polymeric matrix; and a monovalent cation component which is separately dispersed within the polymeric matrix. The monovalent cation component modulates the release of the incorporated agent from the polymeric matrix.

As used herein, modulated release is defined as the change in the release characteristics of an incorporated agent from a biocompatible polymeric matrix containing a dispersed monovalent cation component which is separate from the incorporated agent relative to a polymeric matrix that does not include the monovalent cation component. Release characteristics include the initial release level of the agent, subsequent agent release levels, the amount of agent released, and/or the extent of the release period. The release characteristics can be modified by selecting the type and concentration of the monovalent cation component that is dispersed in the polymeric matrix. In addition, the particle size of dispersed monovalent cation component can selected to modify the release characteristics.

Polymer Selection

Any biocompatible polymer can be used. As used herein, a polymer or polymeric matrix is biocompatible if the polymer and any degradation products of the polymer, are non-toxic to the recipient and also present no significant deleterious effects on the body of the recipient. The biocompatible polymers can be biodegradable polymers, or non-biodegradable polymers, or copolymers and blends thereof.

As used herein, biodegradable is defined as capable of degrading or eroding in vivo to form smaller chemical species over a period of time between one day and nine months. Degradation can result, for example, by enzymatic, chemical and physical processes. Examples of suitable biocompatible, biodegradable polymers include poly (lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, and copolymers and blends thereof.

Suitable non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

The end-groups of the polymers can be blocked or unblocked. Suitable blocking groups include alkyl groups. Acceptable molecular weights for the biocompatible polymers can be determined by a person of ordinary skill in the art of taking into consideration factors such as the desired polymer degradation rate, physical properties such as mechanical strength, and rate of dissolution of polymer in solvent. Typically, an acceptable range of molecular weight is between about 2,000 and 2,000,000 Daltons (Da). In a preferred embodiment, the polymer is a biodegradable polymer or copolymer. In a more preferred embodiment, the polymer is a poly(lactide-co-glycolide) (PLGA) with a lactide:glycolide ratio of about 1:1 and a molecular weight between about 5,000 Da and 70,000 Da. In a more preferred embodiment, the molecular weight of the PLGA is between about 5,000 Da and 42,000 Da.

Agents to be Incorporated

Agent that can be incorporated into the polymeric matrix include therapeutic, prophylactic, and diagnostic agents. Examples of suitable therapeutic and/or prophylactic agents include proteins, such as hormones, antigens, and growth factors; nucleic acids, such as antisense molecules; and small molecules, such as antibiotics, steroids, decongestants, neuroactive agents, anesthetics and sedatives. Examples of suitable diagnostic agents include radioactive isotopes and radiopaque agents. The polymeric matrices can include more than one incorporated agent.

A therapeutically, prophylactically, or diagnostically effective amount of the agents are incorporated into the polymeric matrices. An effective amount of these agents can be readily determined by a person of ordinary skill in the art taking into consideration factors such as body weight; age; physical condition; therapeutic, prophylactic, or diagnostic goal desired; type of agent used; type of polymer used; initial burst and subsequent release levels desired; and desired release rate. Typically, the polymeric matrices will include between about 0.01% (w/w) and 80% (w/w) of incorporated agent.

The incorporated agent may be in the form of particles, for example, crystalline particles, non-crystalline particles, freeze dried particles, and lyophilized particles. Particles preferably are less than about 20 $\mu$m in size, and more preferably less than about 5 $\mu$m. The particles also may include a stabilizing agent and/or other excipient.

Monovalent Cation Component

A monovalent cation component, as defined herein, is a component containing at least one kind of monovalent cation (having a valence of +1) in a non-dissociated state, a dissociated state, or a combination of non-dissociated and dissociated states. Suitable monovalent cation components include, for instance, substances such as metal salts. It is to be understood that an anion is associated with the cation.

The particle size of the monovalent cation component preferably is less than about 50 $\mu$m and more preferably less than about 20 $\mu$m. Even more preferably, the particle size of the monovalent cation component is less than about 5 $\mu$m. Generally, smaller particle sizes provide better modulation of release of the incorporated therapeutic, diagnostic, or prophylactic agent, than larger ones. If very large particles, such as those 100 micron and larger in size, are used, then the swelling effect of the polymer is diminished and the particles only leach out. However, when the particle size is smaller, the entire polymer system swells. Swelling is the mechanism by which modulation occurs.

A suitable concentration of a monovalent cation component is dispersed within the polymer matrix. Suitable concentrations are those which modulate the release of incorporated agents from the polymeric matrix. The optimum concentration depends upon the polymer, the monovalent cation component and the biologically active agent utilized. Preferably, the concentration of the monovalent cation component is between about 1% and 30% (w/w) of the total weight of the polymer matrix, including the incorporated agent. More preferably, the concentration of the monovalent cation component is between about 1% and 20% (w/w) of the total weight of the polymer matrix. Monovalent cation component concentrations greater than about 50% (w/w) are not preferred, since higher concentrations generally lead to leaching out of the monovalent cation component without polymer swelling.

In one embodiment, the monovalent cation component is substantially soluble in aqueous solutions, such as PBS, HEPES, or alimentary tract fluids. Examples of suitable soluble monovalent cation components include NaCl, NaF, KCl, KF and combinations thereof.

Methods for Preparing the Polymeric Matrix

The polymeric matrix can be prepared by dissolving a suitable polymer in a solvent to form a polymer solution, adding an aqueous solution or dispersion of the monovalent cation composition to the polymer solution, and adding a solution or dispersion of the agent to be incorporated. Addition of the monovalent cation component can be completed before addition of the therapeutic, diagnostic, or prophylactic agent. For example, the polymer solution and the salt solution or particles can be mixed by sonication or agitation, while the agent is incorporated later in the process of forming the polymeric matrix.

In those embodiments in which the polymer is insoluble in aqueous solutions and soluble in organic solvents that are immiscible with water, an emulsion can be formed. Emulsions can be formed, for example, by sonicating, agitating, mixing, or homogenizing these solutions.

In a preferred embodiment, the method includes forming a modulated release polymeric matrix as a thin film. Biodegradable polymers are preferred; PLGA is more preferred. A suitable monovalent cation component is dissolved in distilled water and sonicated into the polymer solution along with a biologically active agent also dissolved in distilled water. A thin film is then solvent cast from the polymer solution and left to dry overnight. The film is then subjected to high vacuum for a period of 4–6 hours to extract any residual solvent. The formation of polymeric matrix films is further described in Example 1.

In another embodiment, the method includes forming a modulated release system via the spray drying process. Alternately, the method includes forming modulated release polymer microspheres via the solvent removal process. Either method forms microspheres, or microparticles, encapsulating the monovalent cation component and biologically active agent within the system.

The type of solvent used to dissolve the polymer will depend on the type of polymer. Suitable solvents for dissolving the polymers include polar organic solvents such as methylene chloride, chloroform, acetone, ethyl acetate, tetrahydrofuran, dimethyl sulfoxide, and hexafluoroisopropanol.

In one embodiment, particles of at least one monovalent cation component are pre-dissolved in distilled water and then dispersed within the polymer solution. At least one biologically active agent is added to the polymer solution separately from the addition of the monovalent cation component solution. The biologically active agent can also be dissolved in distilled water, thereby adding to the polymer and cation component emulsion. The monovalent cation component and the biologically active agent can be added to the polymer solution sequentially, in reverse order, intermittently, or through separate, concurrent additions. A biologically active agent can be suspended in a solution of a monovalent cation component in a solvent before dissolving the polymer in the solvent.

In another embodiment, the monovalent cation component is incorporated into the polymeric matrix after the matrix has been formed and has already incorporated the agent. In an alternate embodiment, the protein or active drug added to the polymer solution can be mixed with an excipient, such as at least one stabilizing agent, as is known in the art.

Determining the Relative Amounts of Incorporated Agent and Monovalent Cation Component The amount of a biologically active agent added to the polymer solution can be determined empirically by comparative in vitro tests of polymeric matrices containing different concentrations of at least one monovalent cation component and of at least one biologically active agent. The amount used will vary depending upon the particular agent, the desired effect of the agent at the planned release levels, and the time span over which the agent will be released.

Types of Delivery Devices

Several types of delivery devices, such as thin films, pellets, cylinders, discs, and microparticles can be prepared from the polymeric matrix, using methods well known to those of skill in the art. As used herein, microparticles are particles having a diameter of less than about one millimeter that include an incorporated agent. The microparticles can have a spherical, non-spherical, or irregular shape. Preferably, the microparticles are spherical.

Microspheres formed by the solvent evaporation process are not contemplated to be within the microspheres disclosed herein, unless they were left for a very short time to harden. Otherwise, the monovalent cation component would leach out of the system during the fabrication of the system.

In another embodiment, the method includes forming a modulated release polymeric matrix as a cylinder or any other shape. A polymer solution and monovalent cation component, in dissolved form, are mixed, for example by sonication, until a fine emulsion is produced. The polymer solution is subsequently cast into a mold of the desired shape. The solvent is then removed by means known in the art until a cylinder or other form, with a constant dry weight, is obtained.

Several other methods of using the polymeric compositions include modulating the physical properties of a method for modifying the water absorption, or hydration capacity, without significantly affecting the rate of polymer degradation. The method includes forming a solution of a polymer and then dissolving a monovalent cation component and sonicating it into the polymer solution. The polymer solution is then solidified to form a polymer matrix wherein the monovalent cation component is dispersed therein. See Example 6 below for a further description of this method of enhancing initial polymer hydration.

The composition can be administered to a human, or other animal, for example, by injection and/or implantation subcutaneously, intramuscularly, intraperitoneally, intradermally, intravenously, intraarterially or intrathecally; by administration to mucosal membranes, such as intranasally or by means of a suppository, or by in situ delivery to provide the desired dosage of a biologically active agent based on the known parameters for treatment of the various medical conditions with the agent.

The compositions and methods of preparation and use thereof described herein are further described by the following non-limiting examples.

EXAMPLE 1

Preparation of Polymer Films Containing Salt

Blocked-PLA/PG (50:50) with a molecular weight of 35,000 Da (Boehringer Ingelheim, Resomer RG503, lot #223808) was used for all studies. The films were produced by a film casting technique. The polymer was thoroughly dissolved in methylene chloride (10% w/v) at room temperature.

Films were prepared using water soluble salts containing monovalent cations. The salts were incorporated in the polymer as an emulsion via probe sonication after predissolving the salt in distilled water. The fabrication procedure is described below.

For each set of control films, one gram of PLA/PG polymer (Boehringer Ingelheim, Resomer RG503, lot #223808, MW=34,000 Da) was dissolved in 10 ml methylene chloride (Fisher Scientific) in a glass scintillation vial. A loading of 0%, 1%, 5% or 25% (w/w) sodium chloride (Sigma, lot 105H02501) pre-dissolved in 200 microliters of distilled water was also added to each vial. For each film composition, a set of tetracycline-loaded films was also made. 5% (w/w) tetracycline, also pre-dissolved in 100 ml of distilled water, was used. The contents of the vials were then sonicated for 60 seconds each and cast into ten circular glass rings on Teflon sheets. Films were air-dried at room temperature for 24 hours before being subjected to high-vacuum for an additional 4 hours to extract any residual solvent.

EXAMPLE 2

Effect of Salt on Drug Release Rates

Figure 1B:
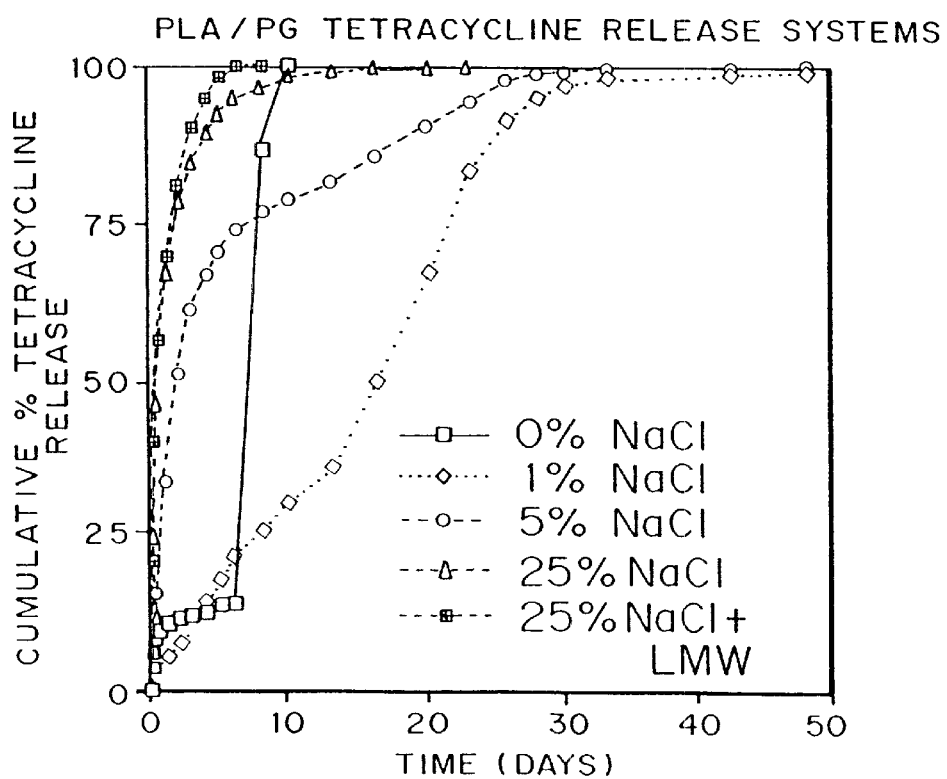

The purpose of this experiment was to test the effect of salt incorporation on drug release from the film samples. Films were immersed in 1.0 M solution of PBS buffer (FTA hemagglutination buffer) at 37° C. for the duration of the study. At regular intervals, the buffer was extracted from the vials and replaced with fresh buffer. The buffer samples were analyzed spectrophotometrically at 354 nm for tetracycline quantification using a Beckman DU-65 spectrophotometer. FIGS. 1A and 1B shows the tetracycline release curves for the various salt loaded systems over the short term (0–5 days) and the long term (0–50 days), respectively.

It is evident from these curves that the soluble salts have a significant impact upon drug release from the polymer films. The control films loaded with 5% tetracycline seemed to follow a typical release pattern for PLA/PG, with an initial release of drug (probably due to diffusion), followed by a plateau phase, another sharp increase in release (possibly due to polymer degradation), and then a second plateau phase. The incorporation of monovalent salts appears to beneficially control the initial burst of drug which occurred in the first few days of release in the control films.

The 1% NaCl system achieved slow, sustained release of tetracycline from the drug-loaded films for periods exceeding six weeks. This system released 12.39% of the drug per day for the first week, decreased to a release of 4.67% of the drug over the next two weeks, and then leveled off at a release rate of 0.01% per day for the last 3 weeks.

The 5% NaCl system also released drug over a six week period, although more of the drug is released in the initial weeks than in the 1% NaCl system or control system. Here, 23.84% of the drug per day came out of the film in the first two days. The rate of drug release then dropped to 0.91% per day from week 1 to week 3. Next, the drug release leveled off at a rate of 0.005% drug release per day from week 6 to week 23 before rising to a rate of 0.05% release per day for the final 3 weeks of the study. Even in this case, the three phase release, as seen in the control samples (0% NaCl), was not observed.

The use of 25% salt resulted in an increased release rate, with the majority of the drug diffusing from the film within the first three weeks. The rate of release was measured at 58.27% per day for the first day, decreased to 0.76% per day for the next two weeks, and leveled off at a release rate of 0.003% drug release per day from week 6 to week 20 of the study.

The 25% salt system containing low molecular weight excipient (PLA/PG MW=5,000 Da) resulted in the greatest amount of release, with most of the drug being expelled in one week. 50.85% of the drug load was released per day in the initial 24 hours of the study, followed by a rate of 8.11% release per day for the next two days, and leveling off early at a release rate of 0.0007% per day for weeks 2–15.

The results clearly show that the salt significantly modulates the drug release from the PLA/PG films. Sodium chloride is very water soluble, so one would assume that most of the salt would come out in the first few days. However, this assumption proved inaccurate for the 1% and 5% salt-loaded systems. Therefore, the following experiments were undertaken to further characterize the effects of salt on the release rate of tetracycline.

EXAMPLE 3

Effect of Salts on Pore Formation

Surface morphology of the films was analyzed over time for evidence of pore formation and subsequent film degradation. Scanning electron microscopy (SEM) was performed using a Hitachi S-2700 scanning electron microscope on film surfaces sampled at day 0, 1, 3, 7, 21 and 42 days in buffer. Film samples were frozen and lyophilized, mounted on metal stubs, and sputter-coated with gold-palladium (Polaron Instrument E5100) prior to viewing.

Films with different salt loadings and from various representative time points were examined under scanning electron microscope for changes in surface morphology. The films degraded over time, as indicated by the formation of pores in the polymer matrix. All film surfaces appear smooth and homogeneous at time zero. However, after being immersed in PBS buffer, the pores form on the film surfaces, indicating degradation and/or swelling. At 0, 1, and 3 days, no change in the appearance of the surface of the control films is evident. At 7 and 21 days, the surface of the control film was still relatively smooth and pore-free, although a few minor blemishes appeared. It was not until 42 days that the control film developed actual pores 5–10 $\mu$m in diameter, which appeared rough and in a beehive-like configuration.

In the 1% NaCl-loaded system, small irregularities in the smooth surface appeared at days 1 and 3. By 7 days, the surface was covered with pinholes 1–5 $\mu$m in size. These pores increased to 5 μm in size by 21 days and resulted in a rough and rugged, degraded appearance by 42 days.

Similarly, the 5% NaCl-loaded system remained pore-free at 1 day, but had small pinholes 1–5 μm in size in its smooth surface by 3 days. At 7 and 21 days, the film was homogeneously covered with distinct pores 5–10 μm in size. After 42 days in buffer, however, the film surface degraded away completely, leaving a rough, irregular surface.

The 25% NaCl system formed pinhole pores 1–5 μm in diameter even prior to submersion in buffer. The pores remained this size for days 1 and 3. However, these pores enlarged significantly, resulting in pores up to 20 microns in diameter at 7 days. At this point, the polymer matrix looked much like a beehive. By 42 days, the surface was again rough and irregular in appearance, as if the structural integrity of the 'beehive' had broken down.

Lastly, the high and low molecular weight blend system with 25% NaCl had small pores over the entire surface at days 0, 1 and 3 days. By 7 days, the film was covered with 30 micron pores. This system degraded too rapidly after this time for further measurements to be taken accurately.

EXAMPLE 4

Effect of Salts on Molecular Weight

Gel permeation chromatography (GPC) on a Perkin Elmer liquid chromatography system was used to determine molecular weights and molecular weight distributions via size-exclusion chromatography. The Perkin Elmer system consisted of an Isocratic LC pump model 250, LC-30 RI detector, LC column oven model 101, and 900 series computer interface box. Samples were lyophilized, dissolved in HPLC-grade chloroform and filtered with a 0.2 micron syringe filter before injecting to remove any insoluble particulates. The samples were then passed through a PL gel 5 micron mixed column and a 5 micron/50 angstrom column at a flow rate of 1.0 ml/min and a temperature of 40° C. All samples were compared to polystyrene standards (Polysciences) ranging in molecular weight from 1000 to 1,860,000 Da. Turbochrom and TC*SEC software programs from Perkin Elmer were utilized for data analysis. Polymer films were sampled at each of the specified time points, including 0, 1, 3, 7, 21 and 42 days.

Figure 2:
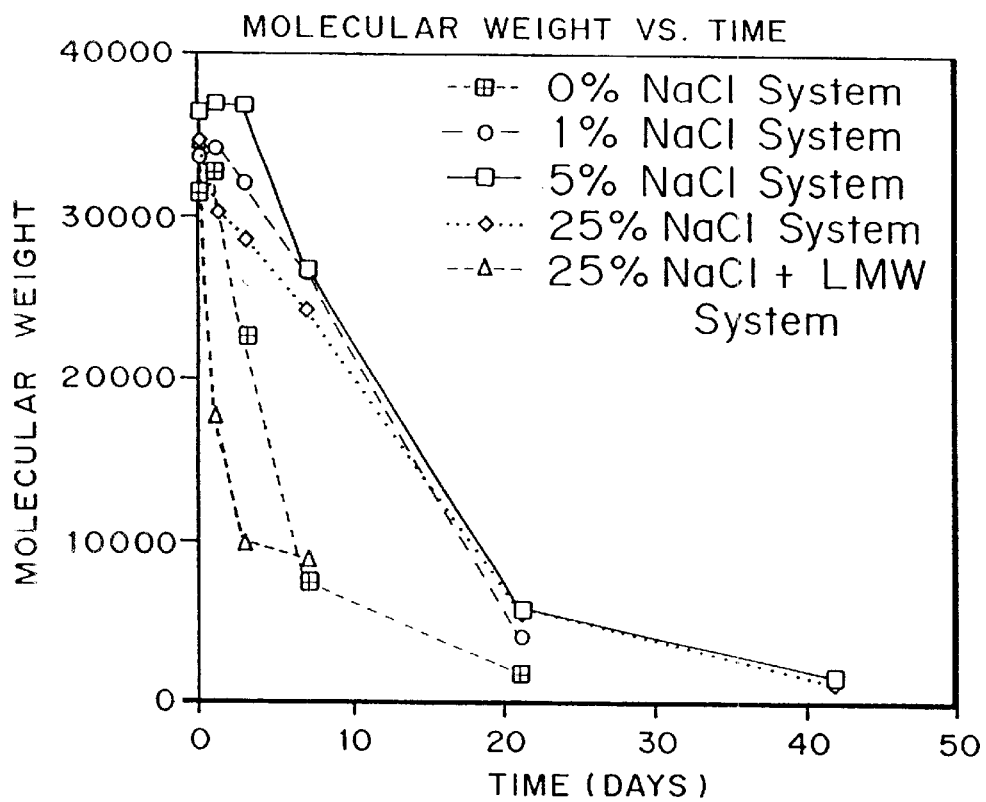
FIG. 2 is a plot of molecular weight (Daltons) as a function of time (days) for polymer films incubated in PBS buffer at 37° C. Grey squares represent a blank PLGA film. Circles represent PLGA film containing 1% NaCl. Dark squares represent PLGA film containing 5% NaCl. Diamonds represent PLGA film containing 25% NaCl. Triangles represent PLGA film containing 25% NaCl and low molecular weight (LMW) polymer excipient.

Tables 1 and 2 indicate degradation of the films as monitored by GPC. The molecular weights decreased as time in buffer increased. Despite the variation in salt loading, the basic trend in molecular weight decrease is similar in most salt systems, except for the polymer blend system. Soluble salts added to the system have very little effect on trends of molecular weight decrease. The blend system, however, utilized a low molecular weight excipient to hasten degradation, speed up release, and appeared to degrade the fastest, as the molecular weight was no longer measurable after one week in buffer. The 5% and 25% NaCl systems, on the other hand, seemed to decrease in molecular weight more slowly than the other systems. FIG. 2 is a graph showing the change in molecular weight over time for the five different systems, with 0, 1, 5, and 25% NaCl, and also 25% NaCl with a low molecular weight excipient. It is evident from the data that the tetracycline-loaded films follow the same pattern as the control films.

TABLE 1

GPC Molecular Weights of Salt-loaded PLA/PG Control Films

| # Days in Buffer | 0% NaCl | 1% NaCl | 5% NaCl | 25% NaCl | 25% NaCl + LMW |
|---|---|---|---|---|---|
| 0 | 31,439 | 33,604 | 36,304 | 34,738 | 34,631 |
| 1 | 32,572 | 34,253 | 36,882 | 30,355 | 17,754 |
| 3 | 22,687 | 32,045 | 36,761 | 28,619 | 9,816 |
| 7 | 7,122 | 26,500 | 26,632 | 24,254 | 8,649 |
| 21 | 2,140 | 3,911 | 5,783 | 5,430 | * |
| 42 | 1,129 | * | 1,522 | 997 | * |

*There was not enough sample remaining to properly analyze.

TABLE 2

GPC Molecular Weights of Salt and Tetracycline-loaded PLA/PG Films

| # Days in Buffer | 0% NaCl | 1% NaCl | 5% NaCl | 25% NaCl | 25% NaCl + LMW |
|---|---|---|---|---|---|
| 0 | 50,534 | 36,161 | 39,661 | 34,303 | 34,017 |
| 1 | 44,463 | 34,415 | 38,837 | 29,951 | 17,751 |
| 3 | 37,159 | 31,465 | 33,370 | 29,791 | 10,947 |
| 7 | 26,634 | 25,394 | 25,971 | 23,711 | 3,946 |
| 21 | 2,963 | 3,329 | 4,917 | 5,791 | * |
| 42 | * | * | 1,393 | 965 | * |

*There was not enough sample remaining to properly analyze.

EXAMPLE 5

Effect of Salt on Glass Transition Temperature

Differential scanning calorimetry (DSC) was used to determine the glass transition temperature (Tg) of the polymer films. All film samples were lyophilized for 24 hours before DSC was performed on a Perkin Elmer Model DSC 7 connected to a controller model TAC 7/DX (Perkin Elmer). Samples were run for each of the following time points; 0, 1, 3, 7, 21, and 42 days after immersion in PBS buffer. Samples were heated from −20 to 100° C. at a rate of 10° C./min, cooled back down to −20° C. at the same rate, and finally heated to 100° C., again at 10° C./min. Glass transition temperatures were calculated from the second heating ramp and examined for shifting trends which would indicate the occurrence of film degradation. Analysis was performed using the Perkin Elmer Thermal Analysis software.

The glass transition temperature of the control films increased over the first few days, then showed a dramatic decrease over the next few weeks. At day 7, the Tg was below the glass transition of PLA/PG. This correlated with the time at which the molecular weight decreased significantly. However, pores were not visible on the control films under SEM at the 21 day point, which could be explained by the fact that the system collapsed due to the low Tg.

Samples of 1%, 5%, and 25% salt-loaded PLA/PG films, as well as the 25% salt-loaded high and low molecular weight blend, were also lyophilized and subjected to differential scanning calorimetry (DSC). Thermograms were analyzed for changes in glass transition temperature, which would indicate film degradation. In Tables 3 and 4 below, it is evident that very little change occurred in the glass transition temperature in the 1%, 5% and 25% salt systems until the 21 day time point, when the Tg fell below the glass transition of PLA/PG. This is also the time at which the molecular weight of these films, as seen by GPC, dropped dramatically and pores 10–50 microns in diameter were visible under SEM.

Figure 3:
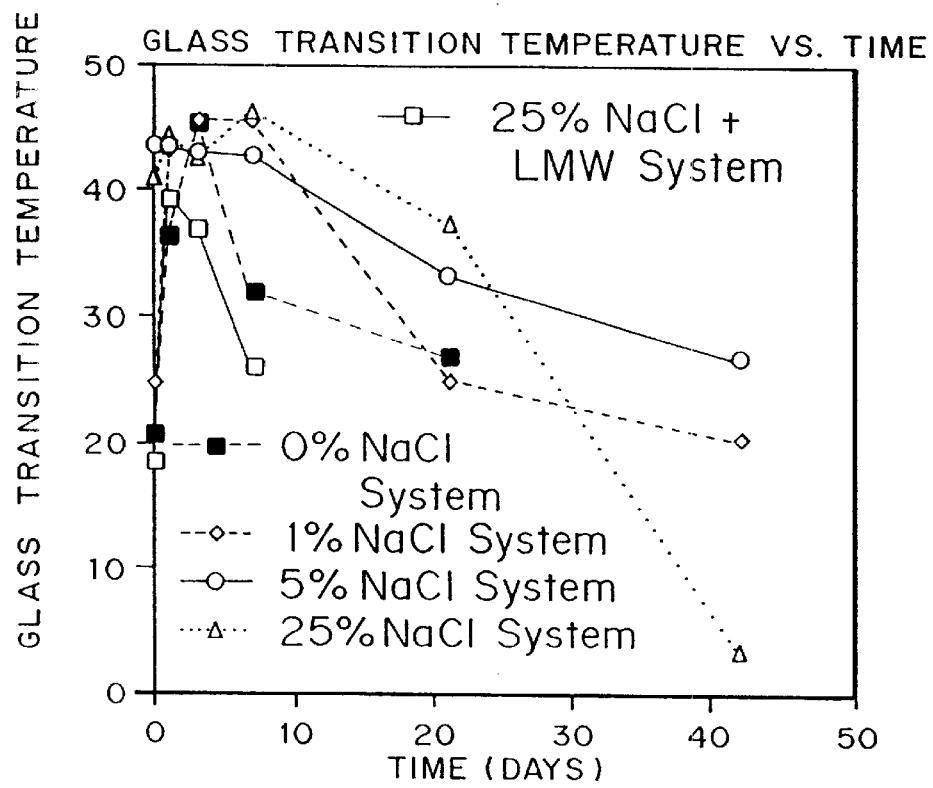
FIG. 3 is a plot of glass transition temperature (° C.) as a function of time (days) for polymer films incubated in PBS buffer at 37° C. Dark squares represent blank PLGA film. Diamonds represent PLGA film containing 1% NaCl. Circles represent PLGA film containing 5% NaCl. Triangles represent PLGA film containing 25% NaCl. Light squares represent PLGA film containing 25% NaCl and LMW polymer excipient.

Although the glass transition of the 25% salt system began dropping at the same time, it was seen to make a more dramatic drop in Tg at 42 days, at which point the molecular weight of the system dropped down to 965–997. Using scanning electron microscopy, it appeared that by 21 days the film was composed primarily of large voids and had likely lost most of its material. At that point, the Tg had dropped below the known glass transition temperature for PLA/PG and descended to a low 3.7° C. by 42 days. The 25% NaCl system with low molecular weight excipient noticeably dropped in Tg by one week, then rapidly degraded such that no further thermograms could be taken. FIG. 3 is a graph illustrating the change in glass transition over time for the various systems. The tetracycline did not seem to impact the system, as the DSC results followed the same trend in both systems.

TABLE 3

DSC Glass Transition Temperatures (° C.)
of Salt-loaded PLA/PG Control Films

| # Days in Buffer | 0% NaCl | 1% NaCl | 5% NaCl | 25% NaCl | 25% NaCl + LMW |
|---|---|---|---|---|---|
| 0 | 20.0 | 24.7 | 43.4 | 41.0 | 18.2 |
| 1 | 36.4 | 42.9 | 43.4 | 44.2 | 39.2 |
| 3 | 45.1 | 45.5 | 42.9 | 42.4 | 36.7 |
| 7 | 31.8 | 45.2 | 42.5 | 46.1 | 25.9 |
| 21 | 26.0 | 25.1 | 33.2 | 37.4 | * |
| 42 | 27.4 | 20.3 | 26.7 | 3.7 | * |

*These samples were degraded too much for accurate thermograms to be taken.

TABLE 4

DSC Glass Transition Temperatures (° C.) of Salt
and Tetracycline-loaded PLA/PG Films

| # Days in Buffer | 0% NaCl | 1% NaCl | 5% NaCl | 25% NaCl | 25% NaCl + LMW |
|---|---|---|---|---|---|
| 0 | 28.6 | 26.2 | 40.7 | 41.0 | 21.2 |
| 1 | 43.8 | 42.8 | 45.2 | 44.4 | 39.5 |
| 3 | 44.9 | 46.1 | 43.4 | 44.0 | 35.8 |
| 7 | 45.2 | 46.6 | 41.5 | 46.5 | 26.9 |
| 21 | 30.6 | 34.7 | 33.7 | 39.0 | * |
| 42 | 30.2 | 19.4 | 25.0 | 10.3 | * |

*These samples were degraded too much for accurate thermograms to be taken.

EXAMPLE 6

Effects of Salts on Polymer Swelling

Figure 4:
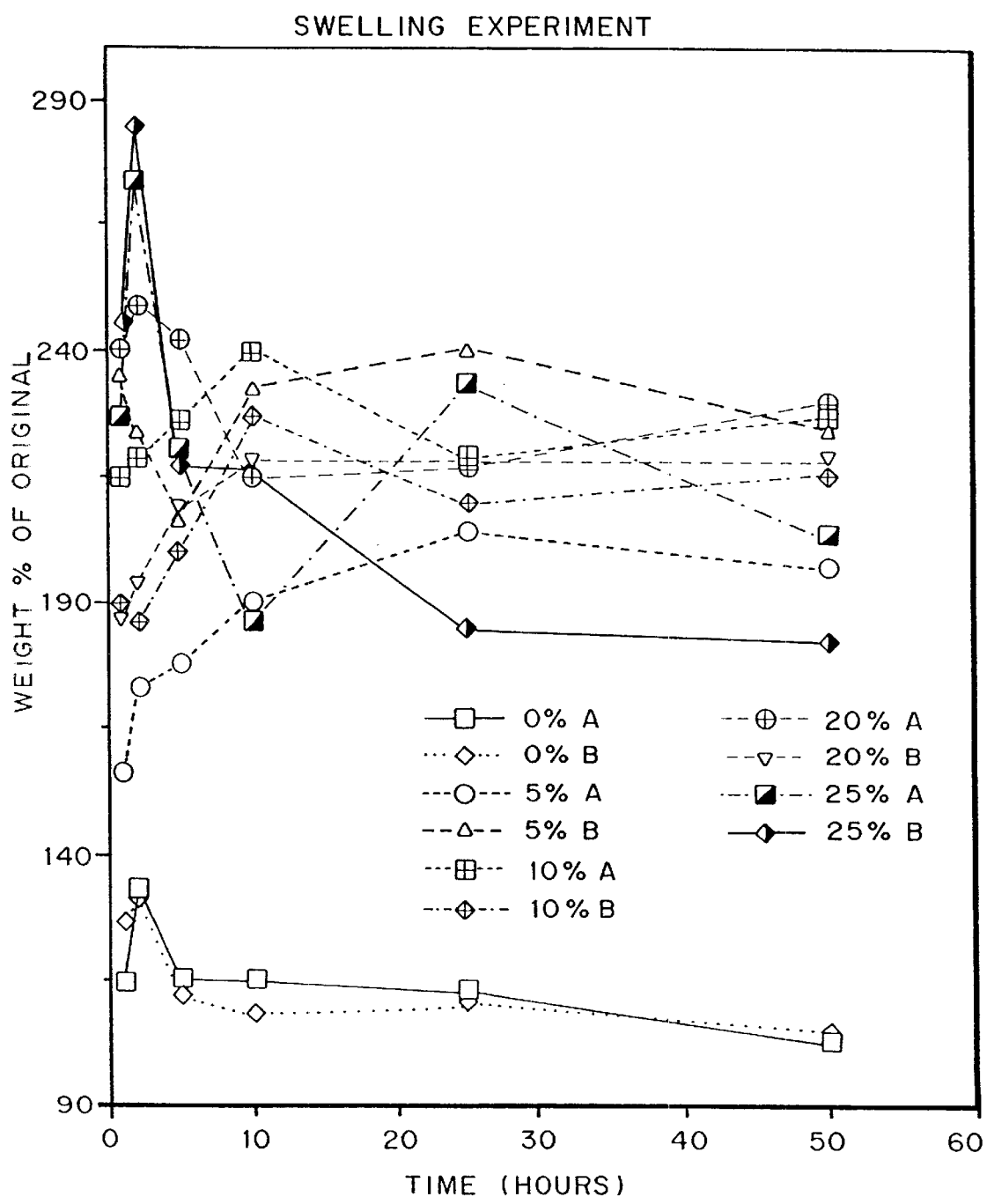
FIG. 4 is a plot of percent of original weight of polymer (%) as a function of time (hours) for PLA/PG polymer films incubated in PBS buffer at 37° C.
Figure 5:
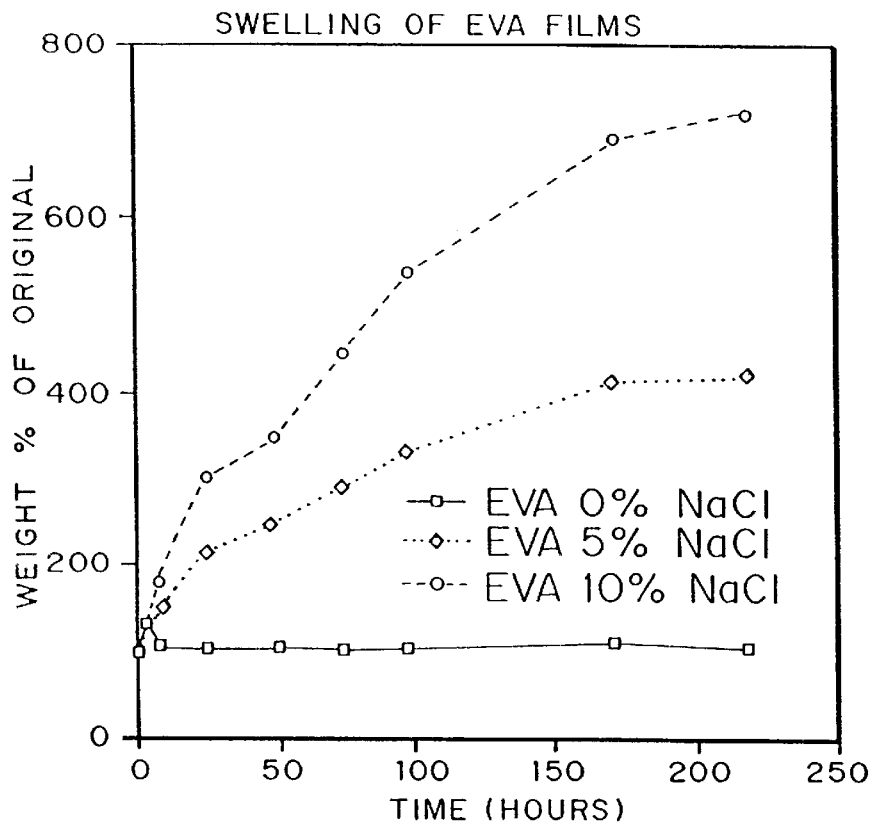
FIG. 5 is a plot of the original weight of polymer (%) as a function of time for EVA polymer films with 0, 5, and 10% NaCl by weight.
Figure 6:
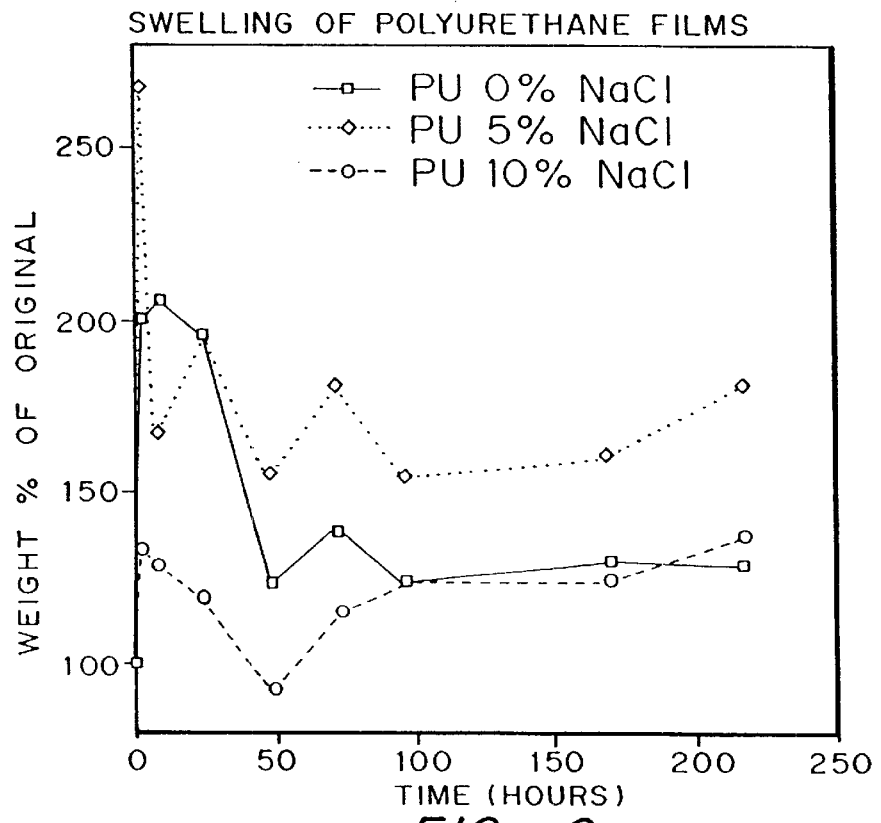
FIG. 6 is a plot of the original weight of polymer (%) as a function of time for polyurethane polymer films with 0, 5, and 10% NaCl by weight.
Figure 7:
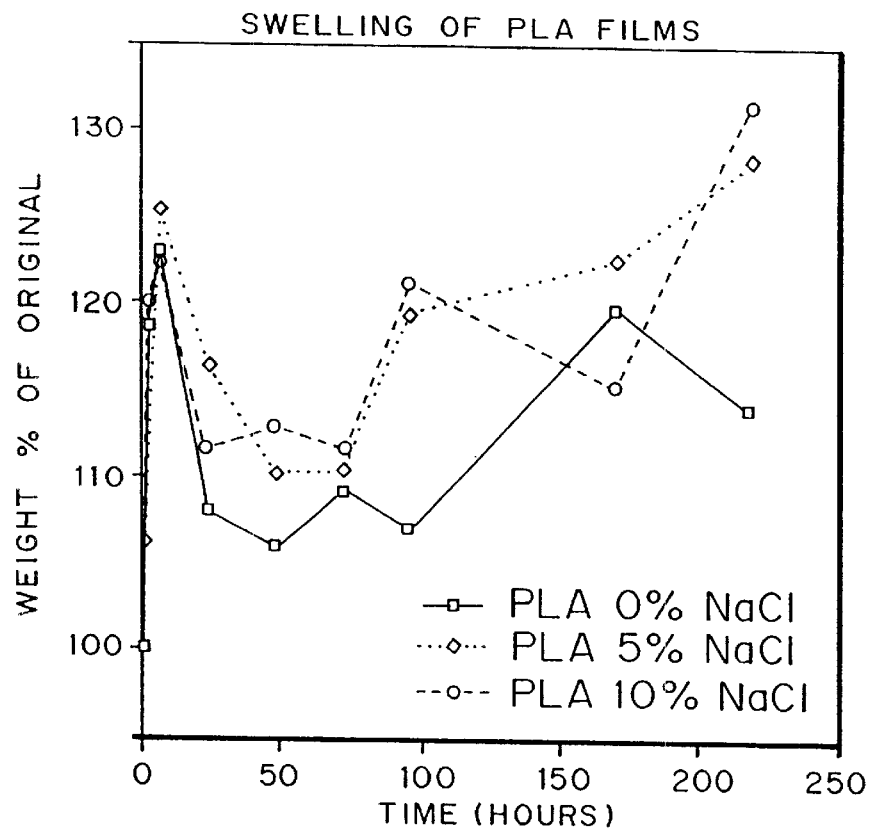
FIG. 7 is a plot of the original weight of polymer (%) as a function of time for PLA polymer films with 0, 5, and 10% NaCl by weight.
Figure 8:
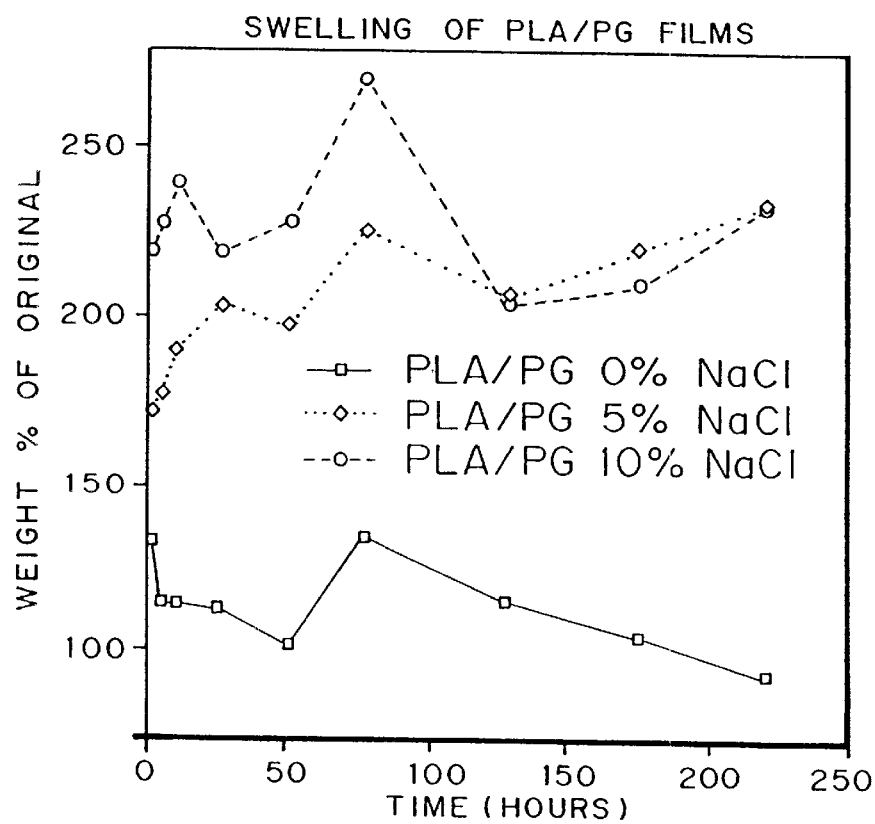
FIG. 8 is a plot of the original weight of polymer (%) as a function of time for PLA/PG polymer films with 0, 5, and 10% NaCl by weight.

Poly (lactide-co-glycolide) films (or PLA/PG films) containing various concentrations of salt, including 0%, 1%, 5%, 10%, 20% and 25%, were preweighed and left to incubate in PBS buffer. At regular intervals, the samples were removed from buffer and weighed. This experiment was performed to investigate the effect of the incorporation of soluble salts on water uptake and swelling of the polymer film. FIG. 4 shows the water uptake of the PLA/PG films with different salt concentrations. Blank films had a small amount of swelling at two hours, and then rapidly returned to their original weight for up to 50 hours. Salt loaded films, on the other hand, demonstrated increased swelling of over 200%, depending on the loading of salt in the system. "A" and "B" indicate two different experiments, and both demonstrate in FIG. 4 that only the salt-loaded films swell appreciably, while the blank films do not.

EXAMPLE 7

Effects of Salts on the Swelling of Various Polymers

Figure 9:
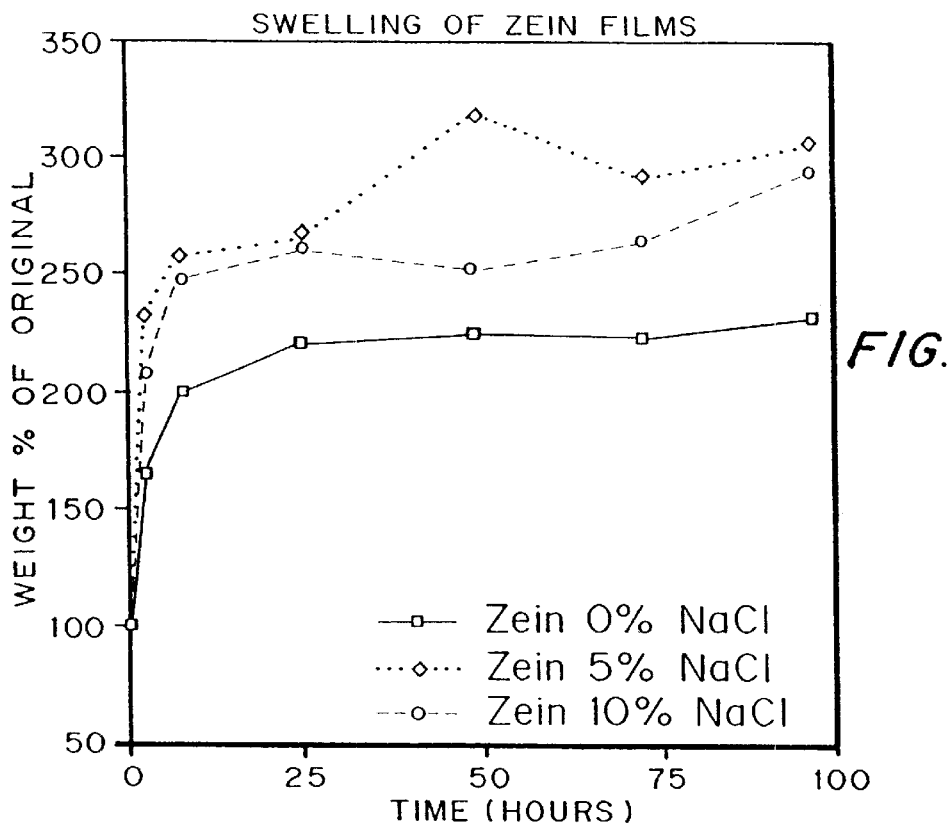
FIG. 9 is a plot of the original weight of polymer (%) as a function of time for zein polymer films with 0, 5, and 10% NaCl by weight.

Polymer films containing 0%, 5%, and 10% concentrations of salt were weighed and left to incubate in PBS buffer. At regular intervals, the samples were removed from buffer, air dried, and weighed. Polymers used in this experiment were ethylene vinyl acetate (MW 235 kDa), Cardiothane (a medical grade polyurethane), poly(lactic acid) (MW 300 kDa), poly(lactide-co-glycolide) (MW 34 kDa), and zein. FIGS. 5–9 show the increased swelling of salt loaded polymer films prepared from EVA (FIG. 5), polyurethane (FIG. 6), PLA (FIG. 7), PLA/PG (FIG. 8), and zein (FIG. 9). The results showed that a significantly greater amount of swelling occurred in rubbery or amorphous polymers, such as ethylene vinyl acetate, as compared to semi-crystalline polymers, such as PLA/PG. For example, PLA did not show significant swelling, possibly indicating that the salts affect amorphous polymeric materials more easily than crystalline polymers.

EXAMPLE 8

Effects of Salt Particle Size on Swelling

Figure 10:
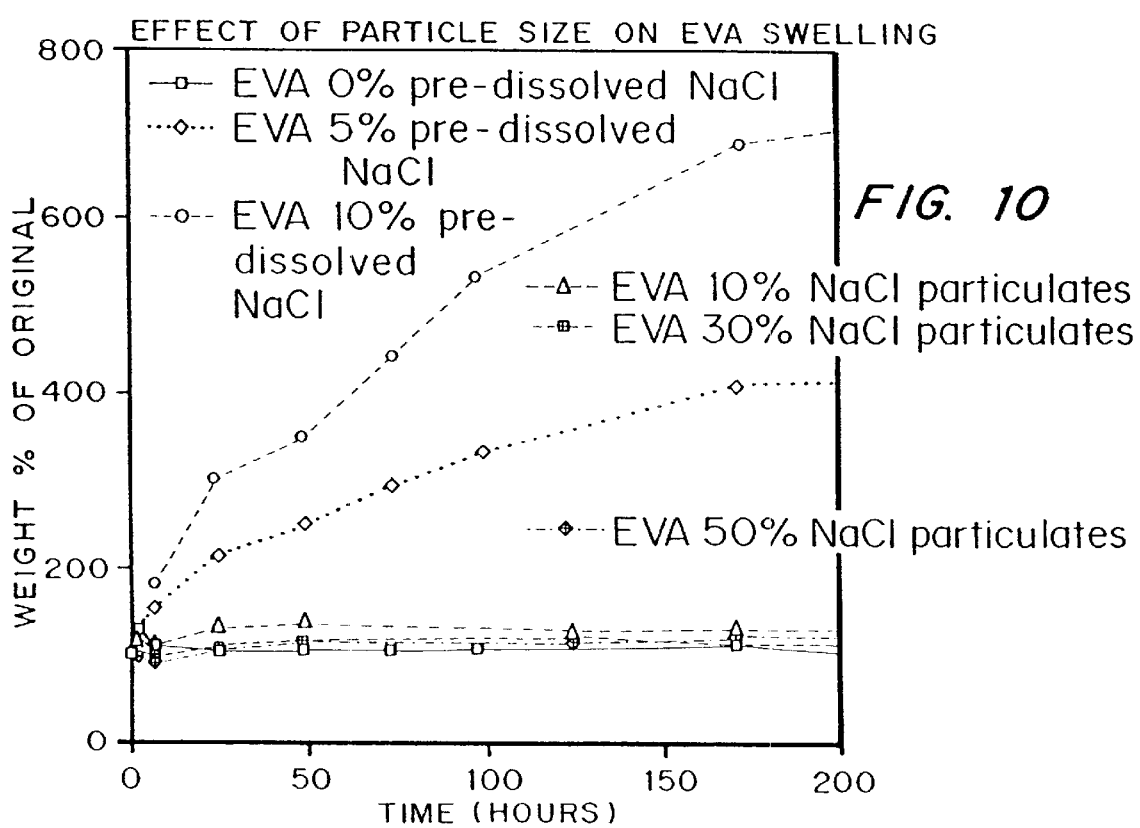
FIG. 10 is a plot of the original weight of polymer (%) as a function of time for EVA polymer films with 0, 5, and 10% pre-dissolved NaCl by weight, and 10, 30, and 50% particulate NaCl by weight.

Another experiment was performed to determine the effect that salt particle size has in the role of water uptake. Ethylene vinyl acetate (EVA) films were made containing 0%, 5%, and 10% loadings of soluble salt that had been pre-dissolved in 200 ml of distilled water and compared to EVA films made containing 10%, 30%, and 50% loadings of soluble salt that had been left as particulates 212 $\mu$m in size. FIG. 10 illustrates the difference in the extent of water uptake that results from varying the salt particle size in a particular polymer. Virtually no swelling occurred in systems loaded with large particles, since they dissolved quickly and leached out of the system, in contrast to small particles that cause the system to swell.

EXAMPLE 9

Evidence of Salt Incorporation by X-RAY Diffraction

X-ray diffraction techniques, performed on a Siemens Diffraktometer D5000, were used to measure film degradation analysis. Samples that had been in buffer for 0, 1, 3, and 7 days were subjected to x-ray and analyzed using DiffracAt computer software for decreasing or disappearing representative crystalline or salt peaks, as well as growth changes of other peaks or amorphous areas. The X-ray diffractometer was also used as a means of determining how long salt remained a part of the system. X-ray diffraction studies on a number of polymers incorporating monovalent salts demonstrated that at least a percentage of the salt remains in the system after more than one week in buffer.

By X-ray diffraction, the salt loading can be measured by looking for a characteristic peak for NaCl in the 32 range on the two-theta axis. The height of this peak increases in size as the loading of salt increases from 5% to 25%, indicating an increase in crystallinity. Similarly, pure PLA/PG polymer has its most pronounced peak appearing at 30, with smaller peaks at 25, 29, 36, 40, 43, 48 and 49. Evidence of salt leaching and decrease in crystallinity was seen as the salt peak for both the 5% and the 25% systems then decreased over time as the salt dissolved and washed out of the system. The decrease in the peak appearing around 32 occurred at day 1, which indicated that salt dissolution begins upon introduction into the buffer solution. The occurrences were most pronounced in the 25% salt system. However, the salt peak in both systems was still evident after one week in buffer, showing that not all of the salt leaches out of the system immediately. This data suggests that the salt is stabilizing the system in some manner, leading to the controlled release.

EXAMPLE 10

Effect of Salt on Protein Release Rates

The purpose of this experiment was to test the effect of salt incorporation on release of proteins (or larger molecular weight species) from film samples. PLGA 50:50 films (Boehringer Ingelheim, Resomer RG 503, lot #223808, MW=34,000 Da) containing 10% RNAse (w/w) and 0%, 5%, or 10% loadings (w/w) of NaCl were made via the solvent casting technique. Films were immersed in 1.0 M solution of PBS buffer (FTA hemagglutination buffer) at 37° C. for the duration of the study. At regular intervals, the buffer was extracted from vials and replaced with fresh buffer. The buffer samples were analyzed using the BCA Protein Assay and spectrophotometric measurement at 562 nm to quantify the amount of RNAse released from the systems over time. FIGS. 11A and 11B show the release curves for the various salt loaded systems over the short term (0–5 days) and the long term (0–40 days), respectively.

The 0% NaCl films (controls) appear to follow a classical release pattern from PLGA, in which there is an initial release of protein, followed by a lag phase, which is followed by a second release beginning around 310 hours, which is likely due to degradation of the polymer. Again, additions of the salts altered this typical triphasic behavior, resulting in more consistent release of protein. The salt also provided for an overall greater amount of protein released. The control film released only about 18% of its protein load in 500 hours, while the 5% and 10% NaCl loaded films released about 55% and 58% of their protein loads in 500 hours, respectively. The results, as shown in FIGS. 11A and 11B, show that addition of the monovalent salt significantly modulates the release of proteins from the PLGA films, despite the much larger molecular weight of the species to be released.

EXAMPLE 11

Swelling of Low Molecular Weight PLGA Microspheres Loaded with 10% NaCl by Weight Microsphere Fabrication Microspheres were made from low molecular weight PLGA (MW=5,800 Da) using a modified solvent removal technique. Particles of sodium chloride (NaCl) were created by spray-drying and crushing with a mortar and pestle, to yield particles less than 5 µm in size. Next, 5 ml of a 10% solution of the PLGA in ethyl acetate and 10% (w/w) NaCl was placed in a separatory funnel with a probe sonicator fitted concentrically within the funnel. The valve on the funnel was adjusted such that pulsed sonication resulted in distinct drops every 4 seconds. Sonication amplitude was set at 20% and was useful in maintaining a homogeneous suspension of salt and polymer. The solution was dropped into a 400 ml glass beaker filled with 100 ml of heavy mineral oil spinning at 1800 rpm with the impeller slightly off-center. After 30 minutes, the speed was slowed to 1400 rpm and 100 ml petroleum ether was slowly dripped in for 4 hours. The resulting microspheres were removed by vacuum filtration.

Swelling Study

Figure 12:
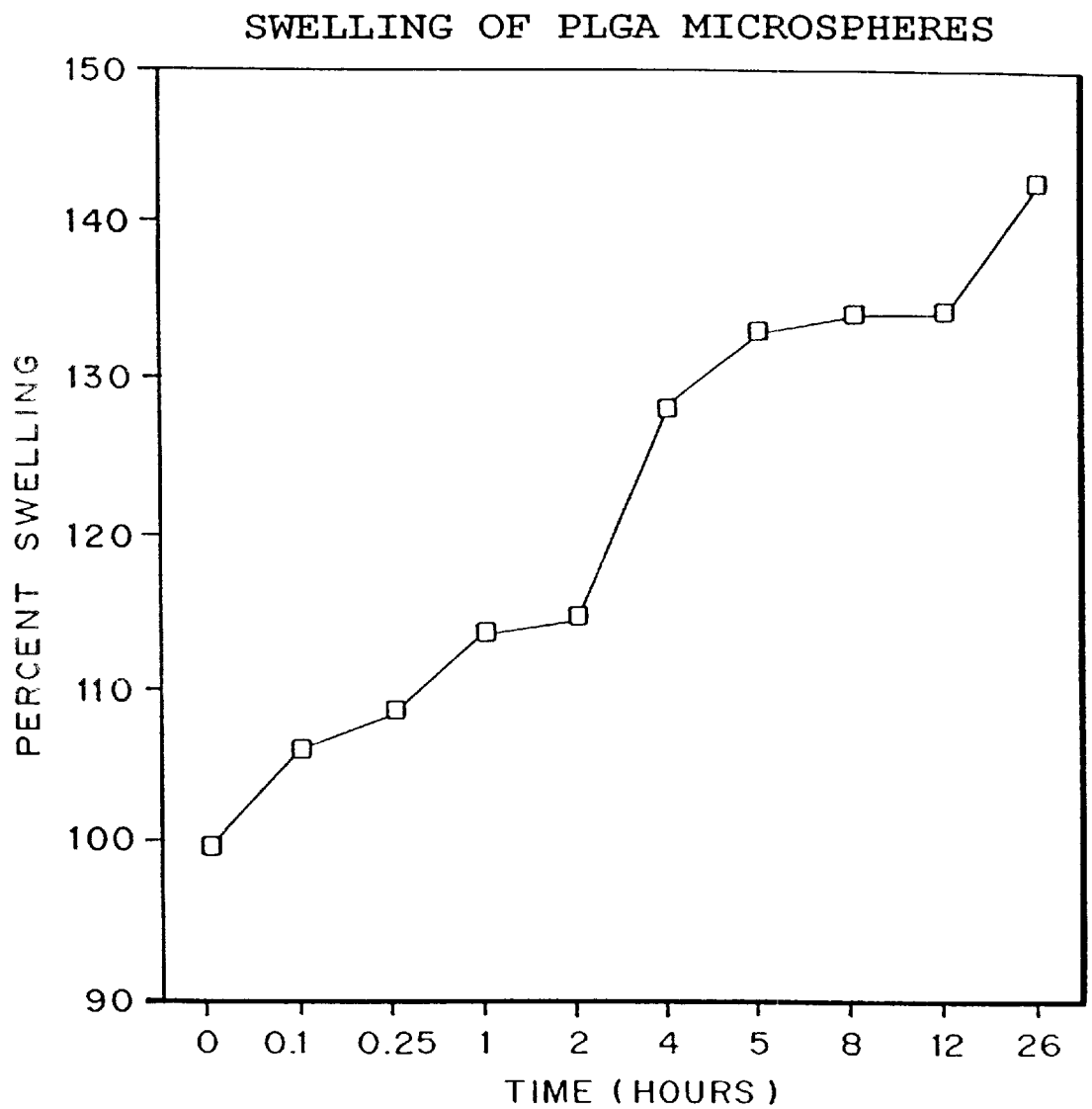
FIG. 12 is a graph showing the percent swelling of PLGA microspheres as a function of time immersed in distilled water for PLGA microspheres loaded with 10% NaCl by weight.

One microsphere was isolated under a stereoscope using forceps and was placed on a slide with a 1 mm graded line. This slide was immersed in a petri dish filled with 20 ml distilled water and was observed using light microscopy and an attached camera. The experiment was done at room temperature, although the light source on the microscope was turned on during picture-taking which could have generated some heat. Pictures were taken at 0.1, 0.25, 1, 2, 4, 5, 8, 12, and 26 hours. The negatives of these pictures were scanned and measured using NIH imaging software. The percent swelling is defined as total area at a certain time point divided by the initial area of the microsphere at t=0. The results are shown in FIG. 12, which indicates significant swelling, especially in the first 5 hours of the experiment.

Modifications and variations of the polymeric matrices and methods of preparation and use thereof will be obvious to those skilled in the art from the foregoing detailed description. Such modifications and variations are intended to come within the scope of the appended claims.

We claim:

1. A composition for the modulated release of a prophylactic, therapeutic, or diagnostic agent, comprising:
   a) a biocompatible and biodegradable polymeric matrix;
   b) an effective amount of a prophylactic, therapeutic, or diagnostic agent dispersed within the polymeric matrix; and
   c) at least one metal monovalent cation for modulating release of the agent from the polymeric matrix, wherein the monovalent cation is obtained from a water-soluble salt and is separately dispersed within the polymeric matrix in the form of particles having a size less than 100 µm, wherein the cation is dispersed in a form and amount effective to swell the polymeric matrix and to provide a defined pattern of release of the agent from the matrix over a period of time between one day and nine months, when the matrix is placed in an aqueous solution.

2. The composition of claim 1 further comprising more than one monovalent cation.

3. The composition of claim 2 wherein both cations are obtained from a water-soluble salt.

4. The composition of claim 1 wherein the cation is obtained from sodium chloride.

5. The composition of claim 1 wherein the polymer further comprises non-biodegradable polymers.

6. The composition of claim 5 wherein the non-biodegradable polymer is selected from the group consisting of polyacrylates, copolymers of polymers of ethylene-vinyl acetates and acyl substituted cellulose acetates, non-degradable polyurethanes, polystyrenes, polyvinyl chloride, polyvinyl fluoride, poly(vinyl imidazole), chlorosulphonate polyolefins, polyethylene oxide, copolymers thereof, and blends thereof.

7. The composition of claim 1 wherein the biodegradable polymer is selected from the group consisting of poly (lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, polyurethanes, copolymers thereof, and blends thereof.

8. The composition of claim 1 wherein the polymer is selected from the group consisting of blocked polymers, unblocked polymers, and blends thereof.

9. The composition of claim 1 wherein the agent comprises a protein.

10. The composition of claim 1 wherein the agent comprises an antibiotic.

11. A composition for the modulated release of a biologically active agent, comprising:
   a) a biocompatible polymeric matrix of a poly(lactide-co-glycolide) polymer;
   b) an effective amount of a biologically active agent dispersed within the polymeric matrix; and
   c) a monovalent cation component for modulating release of the biologically active agent from the polymeric matrix, wherein the monovalent cation component is separately dispersed within the polymeric matrix in the form of particles having a size less than 100 $\mu$m,
wherein the cation is dispersed in a form and amount effective to swell the polymeric matrix and to provide a defined pattern of release of the agent from the matrix over a period of time between one day and nine months, when the matrix is placed in an aqueous solution.

12. The modulated release composition of claim 11 wherein the monovalent cation component is obtained from a salt selected from the group consisting of metal halides.

13. The modulated release composition of claim 11 wherein the biologically active agent is a protein selected from the group consisting of nucleases, erythropoietin, human growth hormone, interferons, interleukins, growth factors, adrenocorticotropic hormone, tumor necrosis factor, and colony-stimulating factors.

14. The modulated release composition of claim 11 wherein the biologically active agent is an antibiotic.

15. The composition of claim 1 wherein the particles of monovalent cation component have a size less than about 50 $\mu$m.

16. The composition of claim 15 wherein the particles of monovalent cation component have a size less than about 20 $\mu$m.

17. The composition of claim 16 wherein the particles of monovalent cation component have a size less than about 5 $\mu$m.

18. The composition of claim 1 wherein the prophylactic, therapeutic, or diagnostic agent is in the form of particles less than about 5 $\mu$m.

19. The composition of claim 1 in a form selected from the group consisting of thin films, pellets, cylinders, discs, and microparticles.

* * * * *